United States Patent [19]

Ruff

[11] Patent Number: 5,593,429
[45] Date of Patent: Jan. 14, 1997

[54] NEEDLE ELECTRODE WITH DEPTH OF PENETRATION LIMITER

[75] Inventor: Leonard H. Ruff, Kennewick, Wash.

[73] Assignee: Cadwell Industries, Inc., Kennewick, Wash.

[21] Appl. No.: 267,428

[22] Filed: Jun. 28, 1994

[51] Int. Cl.$^6$ ............................................. A61M 1/00
[52] U.S. Cl. ........................... 607/116; 128/642; 128/733
[58] Field of Search .................................. 128/642, 418, 128/731, 634, 733, 741, 639, 640, 643; 607/117, 48, 116; 606/44; 604/117

[56] References Cited

U.S. PATENT DOCUMENTS

| | | | |
|---|---|---|---|
| 1,781,362 | 11/1930 | Brigida . | |
| 4,026,301 | 5/1977 | Friedman et al. | 128/418 |
| 4,080,961 | 3/1978 | Eaton | 128/642 |
| 4,295,467 | 10/1981 | Mann et al. | 128/303.18 |
| 4,320,764 | 3/1982 | Hon | 128/642 |
| 4,355,642 | 10/1982 | Alferness | 128/642 |
| 4,374,527 | 2/1983 | Iversen | 128/785 |
| 4,597,620 | 7/1986 | Lindner et al. | 339/89 |
| 4,633,880 | 1/1987 | Osypka et al. | 128/642 |
| 4,644,956 | 2/1987 | Morgenstern | 128/642 |
| 4,658,825 | 4/1987 | Hochberg et al. | 128/634 |
| 4,706,682 | 11/1987 | Stypulkowski et al. | 128/642 |
| 4,892,105 | 1/1990 | Prass | 128/741 |
| 4,969,468 | 11/1990 | Byers et al. | 128/642 |
| 4,998,934 | 3/1991 | Bernstein | 606/44 |
| 5,154,175 | 10/1992 | Gunther | 128/642 |

OTHER PUBLICATIONS

Miscellaneous Electrode Brochures, *Jari Electrode Supply*, Date Unknown.
Chan, Rai Chi et al., "Quantitative Comparison of Motor Unit Potential Parameters Between Monopolar and Concentric Needles", *Muscle & Nerve*, 14:1028–1032, 1991.

*Primary Examiner*—Randall L. Green
*Assistant Examiner*—Perry E. Van Over
*Attorney, Agent, or Firm*—Christensen O'Connor Johnson & Kindness PLLC

[57] ABSTRACT

A needle electrode for use with all types of neurological monitoring equipment. The needle electrode includes a needle portion located at the distal end of the needle electrode. The needle portion is inserted into a patient's muscle to the desired depth in order to perform electromyographic examinations. A shank located at the proximal end of the needle electrode is used to connect the needle electrode to a needle electrode holder and then to monitoring equipment. The needle electrode includes a mid-section located between the needle portion and the shank to regulate the depth to which the needle portion penetrates the patient's muscle, and the depth to which the shank is inserted into a needle electrode holder. The mid-section also maintains the needle electrode holder a specified distance away from the patient's skin to help prevent the needle electrode from being contaminated by the patient's bodily fluids. The mid-section includes a first elongate portion extending approximately normal to the needle portion, adapted to lie adjacent an exterior surface of a patient's skin after the needle portion has been inserted into the patient's skin. A second elongate portion is located at the distal end of the shank and extends approximately normal to the shank to regulate the distance that the shank extends into the needle electrode holder. A third elongate portion located between the first and second elongate portions regulates the distance between the exterior surface of the patient's skin and the needle electrode holder.

21 Claims, 4 Drawing Sheets

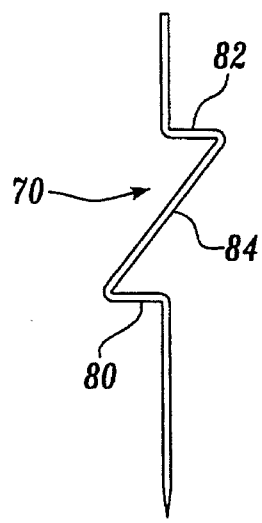
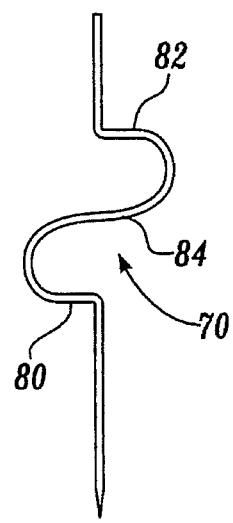
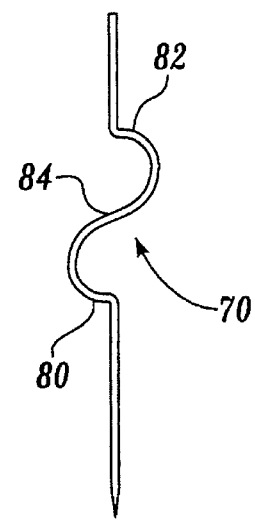
Fig. 3A  Fig. 3B  Fig. 3C
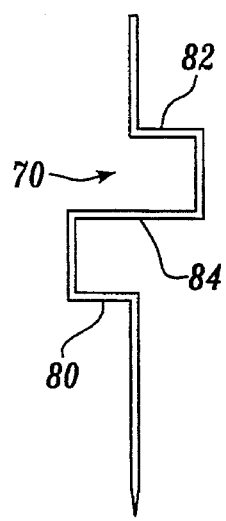
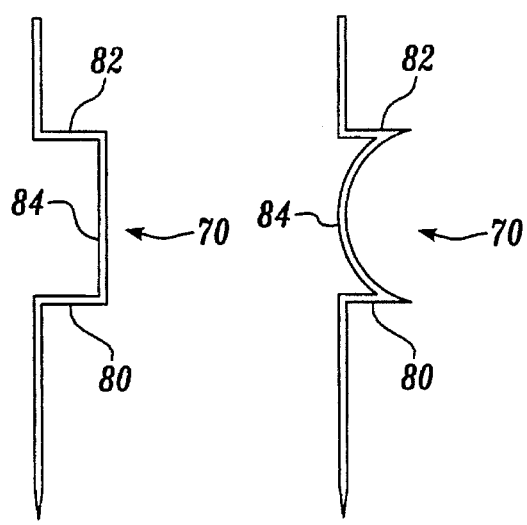
Fig. 4A  Fig. 4B  Fig. 4C  Fig. 4D

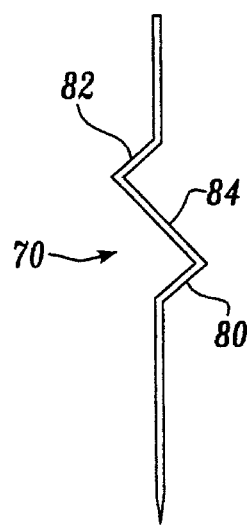
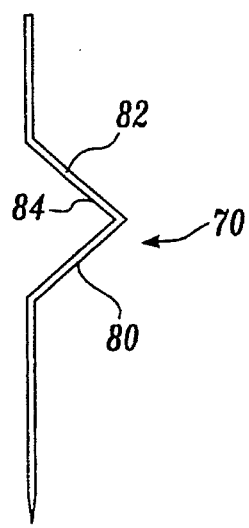
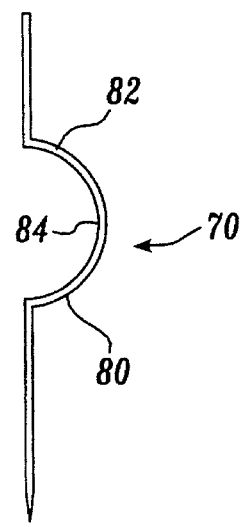
Fig. 5A    Fig. 5B    Fig. 5C
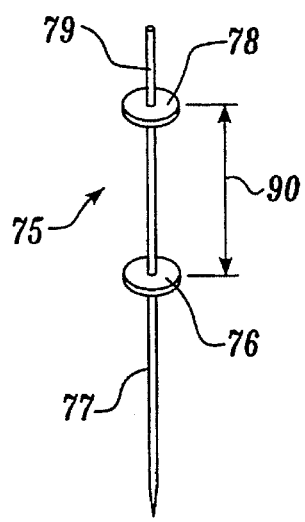
Fig. 6

NEEDLE ELECTRODE WITH DEPTH OF PENETRATION LIMITER

FIELD OF THE INVENTION

The present invention relates to needle electrodes; specifically, the present invention relates to needle electrodes for use in electromyographic examinations.

BACKGROUND OF THE INVENTION

Needle electrodes are designed for use in neurologic examinations using monitoring equipment, namely EMG monitoring equipment. The needle electrodes are connected to monitoring equipment and then inserted into a patient's muscle at the location that is to be stimulated or probed. As a needle electrode is inserted into a patient's body, both the needle electrode and the operator may be exposed to bodily fluids carrying infectious diseases. Because of the danger associated with exposure to bodily fluids, the Food and Drug Administration (FDA) has stringent requirements regarding packaging, sterilization, reuse, disposal and testing performed using needle electrodes.

FDA requirements have resulted in two types of needle electrodes being used in the marketplace. The first type of needle electrode generally used is a disposable needle electrode assembly including a needle electrode, lead wires, and electrical connectors all joined to form a single unit. The needle electrode assemblies are generally sterilized and prepackaged for a one-time use by a physician. The physician opens the sterilized package, connects the needle electrode assembly to the appropriate monitoring equipment, and inserts the needle electrode into a patient's muscle. After completing testing, the entire needle electrode assembly is disconnected from the monitoring equipment and discarded.

Disposable needle electrode assemblies are expensive and highly wasteful of resources due to their one-time use. Disposable needle electrode assemblies also add to the quantity of medical waste produced, increasing waste disposal costs. Because disposable needle electrode assemblies are prepackaged for a specific use, i.e., specific needle size, length, etc., a hospital must stock large numbers of needle electrode assemblies having different sizes and lengths, adding to inventory overhead and storage costs.

The second type of needle electrode assembly commonly used is a reusable needle electrode assembly designed to be sterilized after each use. Similar to disposable needle electrode assemblies, reusable needle electrode assemblies are generally manufactured as a single piece unit including electrical connectors, leads, and needle electrode. Reusable needle electrode assemblies are not as wasteful of resources; however, they are expensive and time-consuming to use due to the complex procedures necessary to sterilize the needle electrode assemblies prior to each use. As with disposable needle electrode assemblies, reusable needle electrode assemblies are generally manufactured as a single unit having a needle electrode of a specific size and length, thus requiring a hospital to stock a wide variety of needle electrode assemblies.

In order to reduce some of the disadvantages of prior needle electrode assemblies, applicant invented a reusable needle electrode assembly that can releasably engage and hold needle electrodes of various configurations. See U.S. Pat. No. 5,482,038 filed concurrently and titled "Needle Electrode Holder." (Attorney docket number CADL-1-7440). To prevent applicant's new needle electrode holder from contacting a patient's skin and thus possibly a patient's bodily fluids during use, a needle electrode configuration that prevents the needle electrode holder from contacting a patient's body or fluids is desired. Preventing the needle electrode holder from coming into contact with a patient's body and bodily fluids eliminates the need to sterilize the holder, decreasing the time and costs associated with using the needle electrode holder. As will be better understood from the following description, the present invention provides a needle electrode configuration that is designed to prevent a needle electrode holder from contacting a patient's bodily fluids.

In electromyographic examinations, it is important that the distal end of the needle electrode be placed within the patient's muscle at the proper position. In the past, physicians have used trial and error to insert a needle electrode into the patient's body to the desired depth. Once inserted, it is common for a patient to move, which often causes the needle electrode to move deeper into the patient's muscle, beyond the desired depth. As will be better understood from the following description, the present invention provides needle electrodes configured in a way that regulates the depth of insertion of the distal end of the electrode into the patient and prevents the needle electrode from moving further into the patient during testing.

SUMMARY OF THE INVENTION

In accordance with the present invention, a needle electrode for use with all types of neurological monitoring equipment is provided. A needle electrode formed in accordance with the present invention includes a needle portion located at the distal end of the electrode. The needle portion is inserted into a patient's muscle to the desired depth during electromyographic examinations. A shank located at the proximal end of the needle electrode connects the needle electrode to a needle electrode holder and, thus, to monitoring equipment. The shank may be used to fixedly connect the needle electrode to a needle electrode holder or it may be used to releasably connect the needle electrode to a needle electrode holder. The needle electrode also includes a mid-section located between the needle portion and the shank that regulates the depth to which the needle portion penetrates a patient's muscle and the depth to which the shank is inserted into the needle electrode holder. The mid-section also maintains the needle electrode holder a specified distance away from the patient's skin to help prevent the needle electrode from being contaminated by the patient's bodily fluids.

In accordance with further aspects of the invention, the mid-section located between the needle portion and the shank of the needle electrode, is elongate and orthogonally intersects the needle portion. The needle portion is adapted to be inserted into a patient's muscle up to the point of intersection. Thus, the elongate mid-section lies adjacent the exterior surface of the patient's skin after the needle portion has been inserted into the patient's skin. The depth to which the needle portion penetrates the patient's muscle is regulated by the location of the point of intersection. The elongate mid-section separates the shank, which is inserted into the needle holder, from the skin. Thus, the needle holder is separated from body fluids emitted by the skin.

In accordance with other aspects of the invention, the elongate mid-section also orthogonally intersects the shank. The second intersection point regulates the depth that the shank may be inserted into the needle electrode holder. A distance between the point of intersection between the needle portion and the mid-section and the point of intersection between the shank and the mid-section regulates the distance between the exterior surface of the patient's skin and the electrode holder when the needle portion is inserted into the patient's muscle.

In some embodiments, the elongate mid-section includes straight portions that lie transverse (preferably normal) to the needle portion and the shank. In other embodiments, the elongate mid-section includes curved portions that transversely intersect the needle portion and shank. The mid-section of other embodiments include both straight and curved portions.

A needle electrode formed in accordance with the present invention allows a physician to easily insert the needle electrode into a patient's body to a predetermined depth and prevents the needle electrode from being inserted into the patient's body beyond the predetermined depth. A needle electrode formed in accordance with the present invention also prevents the shank of the needle electrode from being inserted into a needle electrode holder beyond a predetermined length. In addition, the mid-section of a needle electrode formed in accordance with the present invention helps to maintain the needle electrode holder a predetermined distance from the surface of a patient's skin, thus helping to prevent the needle electrode holder from being contaminated by a patient's bodily fluids. Preventing the needle electrode holder from being contaminated by contact with a patient's bodily fluids allows the needle electrode holder to be reused without being sterilized after each use.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a side elevational view of three alternate embodiments of the present invention ranging from a Z-shaped configuration to an S-shaped configuration;

FIG. 4 is a side elevational view of four alternate embodiments of the present invention;

FIG. 5 is a side elevational view of three alternate embodiments of the present invention showing mid-sections having elongate elements that do not extend normal to the shank or needle portion; and FIG. 6 is an alternate embodiment of a needle electrode including two circular disks that extend radially outwardly from the shank and needle portion of the needle electrode.

DETAILED DESCRIPTION OF THE PREFERRED EMBODIMENT

Figure 1:
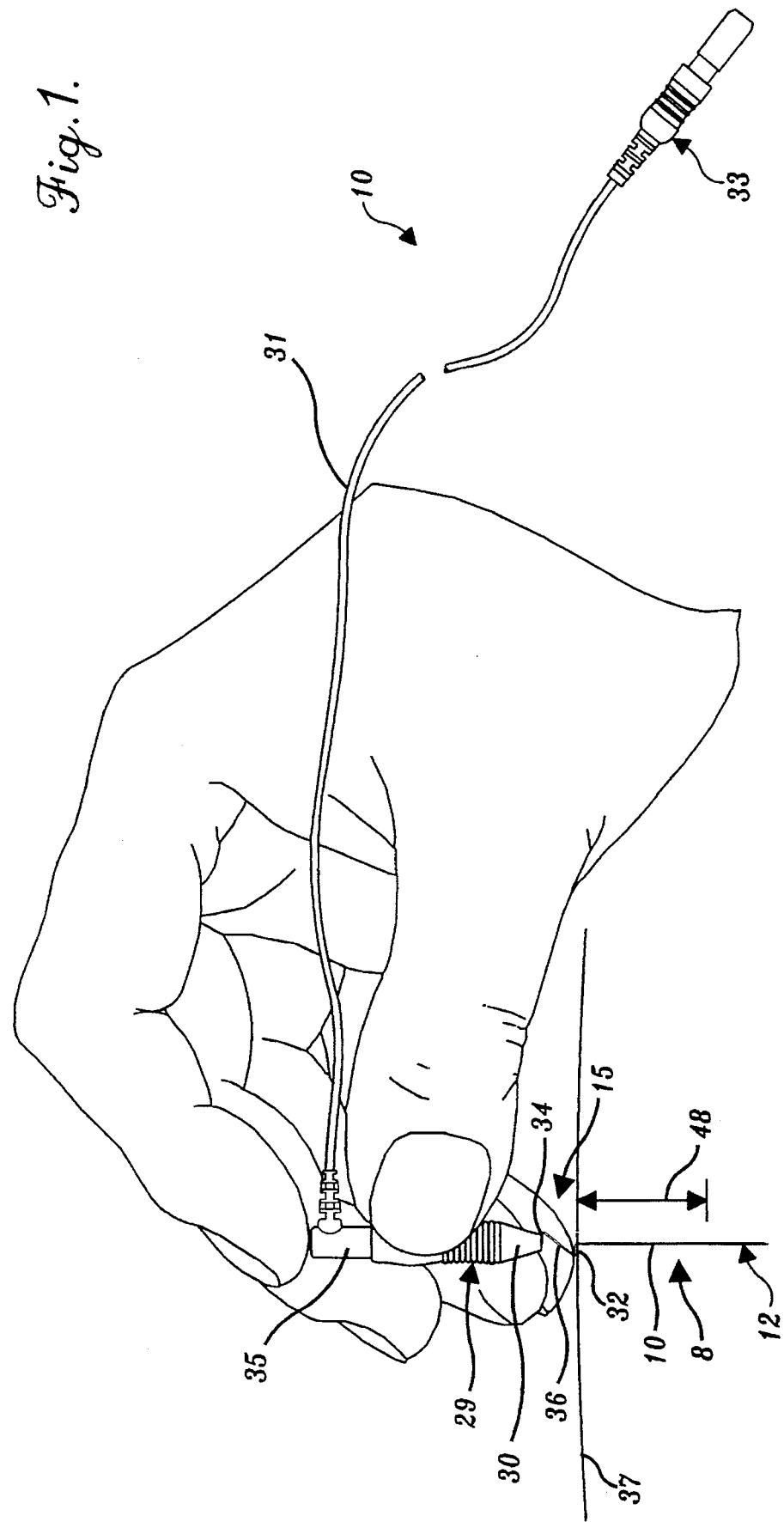
FIG. 1 is a side elevational view of a preferred embodiment of a needle electrode according to the present invention inserted into a needle electrode holder.
Figure 2:
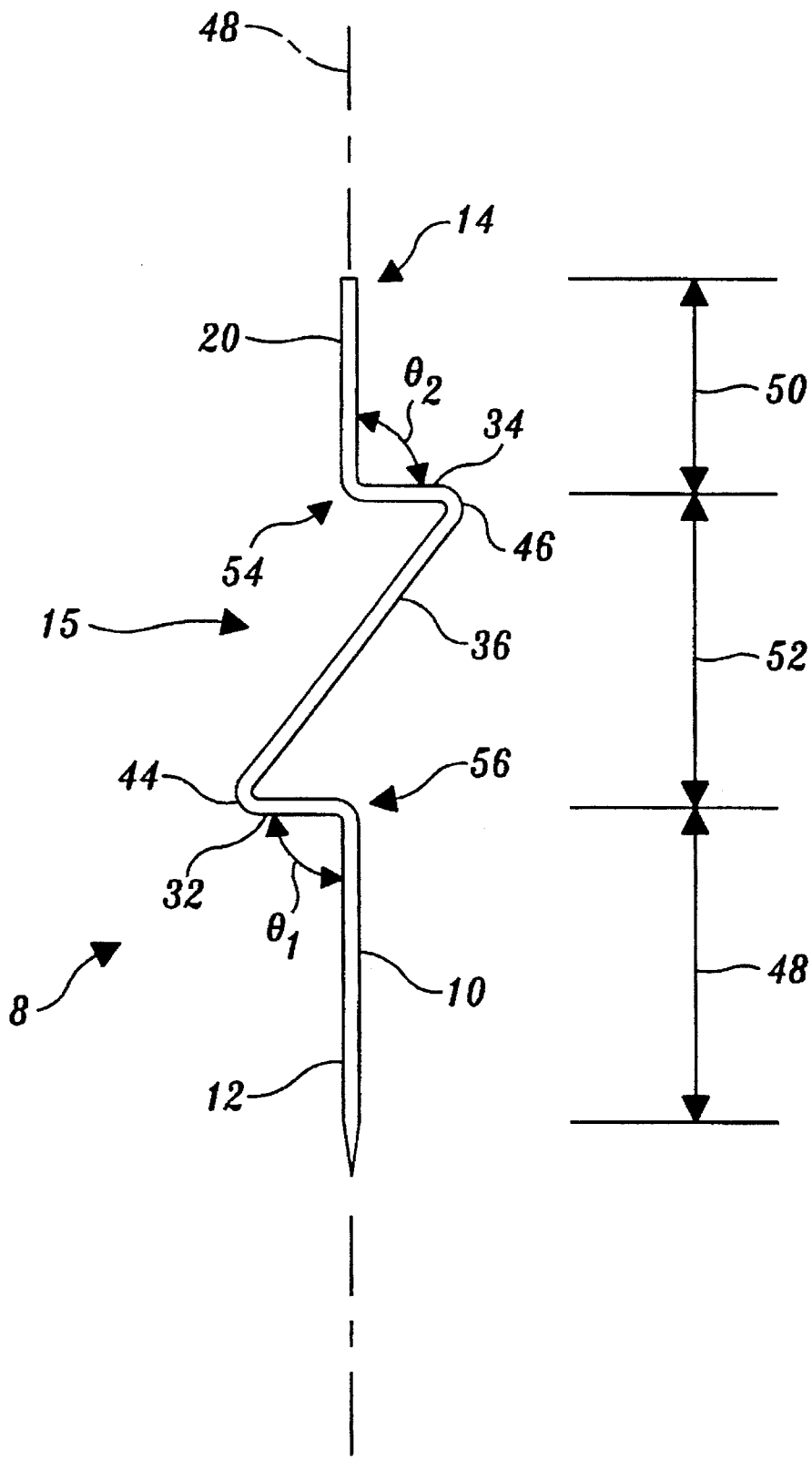
FIG. 2 is a side elevational view of a preferred embodiment of a needle electrode according to the present invention.

A preferred embodiment of a needle electrode 8 according to the present invention is shown in FIGS. 1 and 2. The needle electrode 8 includes an elongated straight needle portion 10 that is located at the distal end 12 of the needle electrode. The needle portion 10 is straight and sized to be inserted through a patient's skin and into a patient's muscle in order to perform electromyographic examinations.

The needle electrode 8 also includes a straight elongated shank 20 (FIG. 2) at the proximal end 14 of the needle electrode. The shank 20 is straight and adapted to be inserted into the tip 30 of a needle electrode holder 29 (FIG. 1), which is connected to monitoring equipment (not shown) through the use of an electrical lead 31 and electrical connector 33. After being inserted into the needle electrode holder 29, the needle electrode 8 is inserted into a patient's muscle by holding the needle electrode holder 29 between the fingers and thumb of a patient's hand 27 and then penetrating the patient's skin with the needle portion 10. Located between the needle portion 10 and the shank 20 is a mid-section 15, described below.

In FIG. 1, the needle electrode 8 is shown used in combination with a releasable needle electrode holder 29. The releasable needle electrode holder 29 releasably engages and disengages the shank 20 by depressing or releasing the base 35 of the needle electrode holder 29. Depressing the base 35 causes a gripping mechanism (not shown) within the needle electrode holder 29 to open and allow the shank 20 to be inserted into the tip 30. Releasing the base 35 causes the gripping mechanism within the needle electrode holder 29 to close and hold the shank 20 after it has been inserted into the tip 30 of the needle electrode holder.

Although the preferred embodiment of the needle electrode 8 is illustrated in use with a specific releasable needle electrode holder 29, it is to be understood that needle electrodes formed in accordance with the present invention could be used with other types of releasable needle electrode holders or with disposable or reusable (after sterilization) one-piece needle electrode assemblies.

The mid-section 15 of the needle electrode regulates the depth 48 to which the needle portion 10 may be inserted into a patient's muscle and the depth 50 that the shank 20 may extend into the needle electrode. The mid-section also regulates a distance 52 between the needle electrode holder and the surface of a patient's skin when the needle electrode is fully inserted into a patient's muscle.

The mid-section 15 of the embodiment of the invention shown in FIGS. 1 and 2 has a Z-shape formed of three straight elongate portions 32, 34 and 36. The first elongate portion 32 extends outwardly from the proximal end 56 of the needle portion 10 approximately normal to the longitudinal axis 48 of the needle portion. The first elongate portion 32 is configured to lie adjacent the exterior surface 37 (FIG. 1) of the patient's skin upon insertion of the needle portion 10 fully into the patient's muscle. The first elongate portion 32 prevents the needle portion 10 from being inserted into the patient's muscle beyond the predetermined depth 48. In order to accurately regulate the depth 48 to which the needle portion 10 is inserted into the patient's muscle, the optimal magnitude of an angle $\theta_1$ (FIG. 2) formed by the needle portion 10 and the first elongate portion 32 is approximately 90°. However, it has been found that magnitudes of $\theta_1$ ranging from 75° to 105° also produce advantageous results. In some applications, it is possible that magnitudes of $\theta_1$ of different angles will also produce advantageous results.

The second elongate portion 34 (FIG. 2) extends outwardly from the distal end 54 of the shank 20 approximately normal to the longitudinal axis 48 of the shank. The second elongate portion 34 is configured to lie adjacent the tip 30 (FIG. 1) of the needle electrode holder 29 when the shank 20 of the needle electrode 8 is fully inserted into the needle electrode holder. The second elongate portion 34 prevents the shank 20 from extending into the needle electrode holder beyond the predetermined distance 50. In order to accurately regulate the distance 50 that the shank 20 extends into the needle electrode holder 29, it is optimal that the magnitude of an angle $\theta_2$ formed by the shank and the second elongate portion 34 be approximately 90°. However, it has also been found that magnitudes of $\theta_2$ ranging from 75° to 105° also produce advantageous results. In some applications, depending on the design of the needle electrode holder, it is possible that other magnitudes of $\theta_2$ will also produce advantageous results.

In the embodiment shown in FIGS. 1 and 2, the first elongate portion 32 extends outwardly from the needle portion 10 in a direction opposite the direction that the second elongate portion 34 extends outwardly from the shank 14. The configuration shown in FIGS. 1 and 2 is preferred because it provides structural symmetry around the central axis 48 (FIG. 2) of the needle electrode 8. Maintaining structural symmetry about the central axis 48 helps to prevent the needle portion 10 from bending or otherwise deforming when the needle portion is inserted into the patient's body.

Alternate embodiments of the needle electrode 8 could include first and second elongate portions 32 and 34 arranged in other configurations. Still other alternate embodiments of the needle electrode could include structures other than the elongate members shown in FIGS. 1 and 2 to regulate the depth of penetration of the needle portion and of the shank. Some alternate embodiments are shown in FIGS. 3–6 and discussed below.

The third elongate portion 36 extends between the outer ends of the first and second elongate portions 32 and 34, respectively. In the embodiment of the invention shown in FIGS. 1 and 2, the third elongate portion 36 is approximately straight and is joined to the ends of the first and second elongate portions 32 and 34 at curved intersections 44 and 46, respectively.

In summary, the first, second, and third elongate portions 32, 34, and 36 define a Z-shape mid-section 15 that off-sets the distal end 54 of the shank 20 from the proximal end 56 of the needle portion 10 by a stand-off distance 52. The stand-off distance 52 maintained by the first, second, and third elongate portions 32, 34, and 36 prevents the needle electrode holder 29 (FIG. 1) from contacting the surface 37 of a patient's skin after the needle portion 10 has been inserted into the patient. The stand-off distance 52 helps to prevent the needle electrode holder 29 from being contaminated by a patient's bodily fluids and thus allows the needle electrode holder to be reused without being sterilized between each use.

In the preferred embodiment, the needle electrode 8 is formed of a conductive stainless steel spring wire that is coated with a coating, such as paralene or Teflon®; over the majority of its length to help lubricate the needle portion of the electrode so that it slides easily into the patient's body. The coating also insulates the majority of the length of the needle portion from the patient's body in order to ensure that electrical contact is only made between the patient's body and the distal end of the needle portion over a predetermined distance to ensure accurate measurements. Obviously, other materials can be used to form or coat the needle electrode 8. Thus, it is to be understood that the present invention is not limited to a specific type of needle electrode or coating. Further, the invention may be incorporated in either monopolar or dipolar needle electrodes.

FIGS. 3–5 illustrate a number of alternate embodiments of needle electrodes incorporating the present invention. In each alternate embodiment, the mid-section of the needle electrode is identified by the reference numeral 70. The first elongate portion is identified by the reference numeral 80, the second elongate portion is identified by the reference numeral 82, and the third elongate portion is identified by the reference numeral 84. Features of the alternate embodiments not discussed below are similar to the preferred embodiment and may be understood by reference to the discussion above.

As with the preferred embodiment, in the alternate embodiments, the first elongate portion 80 prevents the needle portion of the needle electrode from being inserted into a patient's muscle beyond a predetermined distance. The second elongate portion 82 prevents the shank of the needle electrode from being inserted into a needle electrode holder beyond a predetermined distance. The third elongate portion 84 maintains a stand-off distance between the first and second elongate portions 80 and 82, respectively, in order to help prevent a needle electrode holder holding the needle electrode from coming into contact with a patient's bodily fluids.

As discussed above, in order to accurately regulate the depth of penetration of the needle portion of the electrode into a patient's muscle, the optimal embodiments of the present invention include first elongate portions 80 that extend approximately normal to the needle portion. However, first elongate portions 80 that extend at other angles with respect to the needle portion as shown in the alternate embodiments may also be advantageously used. Similarly, it is most optimal that the second elongate portion 82 extends approximately normal to the shank of the needle electrode. However, second elongate portions 82 that extend at other angles with respect to the shank as shown in the alternate embodiments may also be advantageously used.

The two left-most embodiments illustrated in FIG. 3 include first and second elongate portions 80 and 82 that extend perpendicular to the needle portion and shank, respectively. Because the first and second elongate portions 80 and 82 extend perpendicular to the respective portions of the needle electrode, they provide a clearly defined intersection that prevents the shank or needle electrode from moving beyond a predetermined point into the patient's body or into the needle electrode holder. Alternate embodiments such as the right-most embodiment illustrated in FIG. 3 and the three embodiments illustrated in FIG. 5 have first and second elongate portions 80 and 82 that extend at angles greater than 90° with respect to the needle portion and shank, respectively. In these embodiments, the first and second elongate portions do not as clearly define an intersection between the needle portion and the first elongate section and the shank and second elongate section. Thus, these embodiments may not regulate the distance that the needle portion extends into the patient's body or the shank extends into the needle electrode holder as accurately as the preferred embodiment.

As shown in the alternate embodiments of FIGS. 3–5, the first, second and third elongate portions 80, 82 and 84 may be formed into a number of different shapes including straight, curved, or reverse curved. The embodiment shown in FIG. 2 is preferred because it is symmetrical around the axis 48 of the needle electrode, provides a clear intersection between the needle portion 10, shank 20 and mid-section 15, and is also relatively easy to fabricate. Some of the alternate embodiments include tight radiuses of curvature between the first and second elongate portions 80 and 82 and the third elongate portion 84 making them more difficult to fabricate than the preferred embodiment. Other of the alternate embodiments do not have as clearly defined intersections between the needle portion, shank and mid-section; thus, they are not as optimal as the preferred embodiment shown in FIG. 2.

The three alternate embodiments shown in FIG. 5 are not as advantageous as the preferred embodiment because the first and second elongate portions 80 and 82 do not define a clear intersection between the needle portion and the first elongate portion and the shank and the second elongate section. Thus, these three embodiments may not be capable of as great accuracy in regulating the depth of penetration of the needle portion or the depth of insertion of the shank into a needle electrode holder as the preferred embodiment.

Although the preferred embodiment and the alternate embodiments include both first and second elongate portions to regulate both the depth that the needle portion extends into a patient's muscle and the distance that the shank extends into an electrode holder, alternate embodiments could include only the first elongate portion or only the second elongate portion and need not include both. Such alternate embodiments could be used in applications that require only the depth of penetration to be regulated or only the depth that the shank extends into the holder to be regulated.

FIG. 6 illustrates yet another alternate embodiment of the present invention. In FIG. 6, instead of using elongate portions as shown in the other embodiments, the mid-section 75 is formed using two circular disks 76 and 78. The first circular disk 76 extends radially outwardly from the proximal end of the needle portion 77 while the second disk 78 extends radially outwardly from the distal end of the shank 79. The second disk 78 is spaced a distance 90 away from the first disk 76 along the length of the needle electrode in order to define the distance that the mid-section spaces the needle electrode holder from the surface of the patient's skin during operation. Upon insertion into a patient, the first disk 76 lies adjacent the surface of the patient's skin, thus preventing the needle portion 77 from being inserted beyond a predetermined distance. The second disk 78 prevents the shank 79 from being inserted into a needle electrode holder beyond a predetermined distance.

While the preferred embodiment of the invention has been illustrated and described, it will be appreciated that various changes can be made therein without departing from the spirit and scope of the invention. As an example, although various embodiments of the present invention have been illustrated, needle electrodes using mid-sections having other configurations than those shown could be used.

The embodiments of the invention in which an exclusive property or privilege is claimed are defined as follows:

1. A needle electrode for insertion into a patient's muscle, the electrode comprising:
   (a) a single elongate needle portion, located at the distal end of the needle electrode, and having sufficient length to be inserted through a single penetration location into a patient's muscle.
   (b) a shank, located at a proximal end of the needle electrode, and used to connect the needle electrode to a needle electrode holder; and
   (c) a mid-section, located between the needle portion and the shank, that lies adjacent an exterior surface of the patient's skin to regulate a depth that the needle portion penetrates the patient's muscle when the needle portion is fully inserted into the patient's muscle and to regulate a depth that the shank extends into the needle electrode holder when the shank is fully inserted into the needle electrode holder, the mid-section including an elongate portion extending outward approximately normal to the shank to regulate the depth that the shank extends into the needle electrode holder.

2. The needle electrode of claim 1, wherein the mid-section includes an elongate portion extending outwardly approximately normal to the needle portion to regulate the depth that the needle portion penetrates the patient's muscle when the needle portion is fully inserted into the patient's muscle.

3. The needle electrode of claim 2, wherein the elongate portion is curved.

4. The needle electrode of claim 1, wherein the mid-section regulates a distance between an exterior surface of the patient's skin and the needle electrode holder when the needle portion is fully inserted into the patient's muscle and the shank is fully inserted into the needle electrode holder to prevent the needle electrode holder from contacting the patient's bodily fluids.

5. The needle electrode of claim 4, wherein the mid-section includes an elongate portion that extends a sufficient distance approximately normal to the patient's skin between the shank and the needle portion to regulate the distance between an exterior surface of the patient's skin and the needle electrode holder.

6. The needle electrode of claim 5, wherein the elongate portion is approximately straight.

7. The needle electrode of claim 5, wherein the elongate portion is curved.

8. The needle electrode of claim 5, wherein the elongate portion is a reverse curve.

9. The needle electrode of claim 1, wherein the needle electrode includes a cylindrical member extending radially outwardly from the shank to regulate the depth that the shank extends into the needle electrode holder.

10. The needle electrode of claim 1, wherein the elongate portion is curved.

11. The needle electrode of claim 1, wherein the mid-section includes a cylindrical member extending radially outwardly from a proximal end of the needle portion.

12. The needle electrode of claim 1, wherein the needle electrode is formed from a continuous length of conductive wire.

13. A needle electrode for insertion into a patient's muscle to a predetermined depth, the needle electrode comprising:
   (a) an elongate shank located at a proximal end of the needle electrode and adapted to join the needle electrode to a needle electrode holder;
   (b) a single elongate needle portion located at a distal end of the needle electrode and adapted to be inserted into a patient's muscle through a single penetration point in the patient's skin;
   (c) a first elongate member, located at a proximal end of the needle portion, and extending approximately normal to the needle portion, the first elongate member being adapted to lie adjacent an exterior surface of the patient's skin when the needle portion is fully inserted into the patient's muscle to regulate the depth that the needle portion extends into the muscle;
   (d) a second elongate member, located at a distal end of the shank, and extending approximately normal to the needle portion, to regulate a depth that the shank extends into the needle electrode holder; and
   (e) a third elongate member extending between the first and second elongate members and maintaining the first and second elongate members a sufficient distance apart to prevent the needle electrode holder from contacting the patient's bodily fluids when the needle portion is fully inserted into the patient's muscle and the shank is fully inserted into the needle electrode holder.

14. The needle electrode of claim 13, wherein the first elongate member is curved.

15. The needle electrode of claim 13, wherein the second elongate member is curved.

16. The needle electrode of claim 13, wherein the third elongate member is curved.

17. The needle electrode of claim 13, wherein the third elongate member forms a reverse curve.

18. The needle electrode of claim 13, wherein the needle electrode is formed from a continuous length of conductive wire.

19. A needle electrode for insertion into a patient's muscle, the needle electrode comprising:

(a) a single elongate needle portion located at the distal end of the needle electrode and having sufficient length to be inserted through a single penetration location into a patient's muscle;

(b) a shank, located at a proximal end of the needle electrode and used to connect the needle electrode to a needle electrode holder; and (c) a mid-section located between the needle portion and the shank, that lies adjacent an exterior surface of the patient's skin to regulate a depth that the needle portion penetrates the patient's muscle when the needle portion is fully inserted into the patient's muscle and to regulate a depth that the shank extends into the needle electrode holder when the shank is fully inserted into the needle electrode holder, the mid-section including an elongate portion extending outward approximately normal to the needle portion to regulate the depth that the needle portion penetrates the patient's muscle when the needle portion is fully inserted into the patient's muscle.

20. A needle electrode for insertion into a patient's muscle, the electrode comprising:

(a) a single elongate needle portion, located at the distal end of the needle electrode, and having sufficient length to be inserted through a single penetration location into a patient's muscle;

(b) a shank, located at a proximal end of the needle electrode, and used to connect the needle electrode to a needle electrode holder; and (c) a mid-section located between the needle portion and the shank that lies adjacent an exterior surface of the patient's skin to regulate a depth that the needle portion penetrates the patient's muscle when the needle portion is fully inserted into the patient's muscle and to regulate a depth that the shank extends into the needle electrode holder when the shank is fully inserted into the needle electrode holder, the mid-section also regulating a distance between an exterior surface of the patient's skin and the needle electrode holder when the needle portion is fully inserted into the patient's muscle and the shank is fully inserted into the needle electrode holder to prevent the needle electrode holder from contacting the patient's bodily fluids, the mid-section including an elongate portion that extends a sufficient distance approximately normal to the patient's skin between the shank and the needle portion to regulate the distance between an exterior surface of the patient's skin and the needle electrode holder.

21. A needle electrode for insertion into a patient's muscle, the needle electrode comprising:

(a) a single elongated needle portion, located at the distal end of the needle electrode and having sufficient length to be inserted through a single penetration location into the patient's muscle;

(b) a shank located at a proximal end of the needle electrode and used to connect the needle electrode to a needle electrode holder; and (c) a mid-section, located between the needle portion and the shank, that lies adjacent an exterior surface of the patient's skin to regulate a depth of the needle portion when the needle portion is fully inserted into the patient's muscle and to regulate a depth that the shank extends into the needle electrode holder when the shank is fully inserted into the needle electrode holder, wherein the needle electrode is formed from a continuous length of conductive wire.

* * * * *